(12) United States Patent
Glahn et al.

(10) Patent No.: US 9,589,307 B2
(45) Date of Patent: Mar. 7, 2017

(54) METHOD OF SELLING ABSORBENT ARTICLES BEARING SIMILAR AND/OR RELATED GRAPHICS

(71) Applicant: The Procter & Gamble Company, Cincinnati, OH (US)

(72) Inventors: Tina Marie Glahn, Cincinnati, OH (US); Beth Goldman Mason, Cincinnati, OH (US); George Christopher Dobrin, Mason, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 273 days.

(21) Appl. No.: 14/468,422

(22) Filed: Aug. 26, 2014

(65) Prior Publication Data

US 2014/0365330 A1  Dec. 11, 2014

Related U.S. Application Data

(62) Division of application No. 12/835,196, filed on Jul. 13, 2010, now Pat. No. 8,996,410.

(51) Int. Cl.
| | |
|---|---|
| *G06F 17/50* | (2006.01) |
| *G06Q 90/00* | (2006.01) |
| *G06Q 30/06* | (2012.01) |
| *G06Q 99/00* | (2006.01) |
| *A61F 13/514* | (2006.01) |
| *A61F 13/551* | (2006.01) |
| *G06K 15/02* | (2006.01) |

(52) U.S. Cl.
CPC ....... *G06Q 90/00* (2013.01); *A61F 13/51496* (2013.01); *A61F 13/55115* (2013.01); *G06F 17/50* (2013.01); *G06K 15/021* (2013.01); *G06Q 30/0621* (2013.01); *G06Q 99/00* (2013.01)

(58) Field of Classification Search
CPC ... G06Q 30/0621; G06F 17/50; G06K 15/021
USPC ........................................................ 705/26.5
See application file for complete search history.

(56) References Cited

U.S. PATENT DOCUMENTS

| 3,842,837 A | 10/1974 | Sward |
| 4,249,532 A | 2/1981 | Polansky et al. |
| 4,615,695 A | 10/1986 | Cooper et al. |
| 4,649,573 A | 3/1987 | Yen |
| 5,503,076 A | 4/1996 | Yeo |
| 5,591,151 A | 1/1997 | Hasse et al. |
| 5,924,131 A | 7/1999 | Wilkinson |
| 6,045,543 A | 4/2000 | Pozniak et al. |

(Continued)

FOREIGN PATENT DOCUMENTS

| EP | 0 547 497 A2 | 6/1993 |
| JP | 2003-070838 A | 3/2003 |

(Continued)

OTHER PUBLICATIONS

International Search Report, PCT/IB2007/054482, mailed Aug. 4, 2008 (14 pages).

(Continued)

*Primary Examiner* — Mila Airapetian
(74) *Attorney, Agent, or Firm* — Andrew A Paul

(57) ABSTRACT

A method of selling absorbent articles wherein the absorbent articles are co-packaged sets of absorbent articles bearing similar and/or related graphics.

14 Claims, 10 Drawing Sheets

(56) References Cited

U.S. PATENT DOCUMENTS

| | | |
|---|---|---|
| 6,219,452 B1 | 4/2001 | Nair et al. |
| 6,297,424 B1 | 10/2001 | Olson et al. |
| 6,307,119 B1 | 10/2001 | Cammarota et al. |
| 6,352,528 B1 | 3/2002 | Weber et al. |
| 6,564,118 B1 | 5/2003 | Swab |
| 6,635,797 B2 | 10/2003 | Olson et al. |
| 6,702,795 B2 | 3/2004 | Klemp |
| 6,859,679 B1 | 2/2005 | Smith et al. |
| 7,189,301 B2 | 3/2007 | Otsubo et al. |
| 7,520,873 B2 | 4/2009 | Sosalla et al. |
| 7,657,340 B2 | 2/2010 | Lind |
| 7,727,353 B2 | 6/2010 | Nair et al. |
| 7,956,234 B2 | 6/2011 | Sosalla et al. |
| 8,231,590 B2 | 7/2012 | Zander et al. |
| 8,236,385 B2 | 8/2012 | Yahiaoui et al. |
| 2003/0130632 A1 | 7/2003 | Costea et al. |
| 2004/0236457 A1 | 11/2004 | Stabelfeldt et al. |
| 2005/0131571 A1 | 6/2005 | Costin |
| 2006/0069372 A1 | 3/2006 | Chakravarty et al. |
| 2006/0173429 A1 | 8/2006 | Acors |
| 2006/0247594 A1 | 11/2006 | Nickel et al. |
| 2007/0032768 A1 | 2/2007 | Cohen et al. |
| 2007/0100692 A1 | 5/2007 | Minifie et al. |
| 2007/0295629 A1 | 12/2007 | Adriaanse et al. |
| 2008/0077415 A1* | 3/2008 | Shannon ............... G06Q 10/101 705/300 |
| 2008/0082071 A1 | 4/2008 | bryant et al. |
| 2008/0097875 A1 | 4/2008 | Kaufman et al. |
| 2008/0108967 A1 | 5/2008 | Mizushima et al. |
| 2008/0234643 A1 | 9/2008 | Kaneda |
| 2009/0247979 A1 | 10/2009 | Sosalla et al. |
| 2009/0260123 A1 | 10/2009 | Swift |
| 2009/0287173 A1 | 11/2009 | Sosalla et al. |
| 2011/0146900 A1 | 6/2011 | Ruman |
| 2012/0016327 A1 | 1/2012 | Mason et al. |
| 2012/0024177 A1 | 2/2012 | Warner et al. |
| 2012/0029457 A1 | 2/2012 | Mason et al. |
| 2012/0030145 A1 | 2/2012 | Mason et al. |

FOREIGN PATENT DOCUMENTS

| | | |
|---|---|---|
| WO | WO 2005-014297 A1 | 2/2005 |
| WO | WO 2007-024327 A1 | 3/2007 |

OTHER PUBLICATIONS

International Search Report, PCT/US 2011/043655, mailed Nov. 22, 2011 (11 pages).

Patty Brown and Janett Rice, Ready-to-Wear Apparel Analysis, UpperSaddle River; Printice Hall, 2001.

* cited by examiner

METHOD OF SELLING ABSORBENT ARTICLES BEARING SIMILAR AND/OR RELATED GRAPHICS

FIELD OF THE INVENTION

In one aspect, the invention relates generally to a method of selling absorbent articles having graphics disposed upon them. The method provides co-packaged sets of absorbent articles bearing similar and/or related graphics.

BACKGROUND OF THE INVENTION

Absorbent articles are used commonly. In many cases, e.g. diapers, the purchaser of the absorbent article is not the end user of the article. Many factors influence the purchaser's decision to purchase particular absorbent articles, non-limiting examples of which include: price and product performance, e.g. absorbency, ease of fastening/refastening, tactile feel against the skin, etc. The aesthetics of an absorbent article have become an increasingly important factor in driving purchase decision-making. Many purchasers prefer to have colors, patterns, and/or other designs employed by the absorbent article. This creates a need to provide desirable graphics without having an unacceptably negative impact on other decision factors, such as price and absorbency.

Conventional methods of designing graphics for absorbent articles may constitute contemplating then adding a border, or simple repeating patterns, e.g. circles or hatch marks, or the method may go so far as to have a graphic designer create a particular design for use with an absorbent article. However, many of these aforementioned methods suffer from one or more disadvantages. For example, the patterns must oftentimes be very simple, e.g. borders, spots, or solid colors, or the patterns take a long time and much effort to get from artistic conception to technical achievement of printing on the absorbent article, and even then, only to yield one or a few designs. Further, typically for a new design, the process must begin from scratch. There is a need to provide more complex and more artistic graphics using less complex and time consuming methods.

Conventional methods of selling absorbent articles typically provide a plurality of absorbent articles in a unit, e.g. polybag or cardboard box, where all the absorbent articles in that unit have identical graphics, if any at all. This method suffers from one or more disadvantages. As noted above, purchasers increasingly prefer absorbent articles with graphics, and it is believed that some purchasers would prefer absorbent articles with a variety of graphics. There is a need to provide absorbent articles with a variety of graphics, preferably similar and/or related graphics, in a single unit or at least units available for purchase together.

SUMMARY OF THE INVENTION

In one aspect, the invention relates to a method of selling absorbent articles wherein the absorbent articles are co-packaged sets of absorbent articles bearing similar and/or related graphics.

It is an object of this invention to provide a method of selling absorbent articles with a variety of graphics, preferably similar and/or related graphics, in a single unit or at least units available for purchase together. These and other objects, features, and advantages of the invention will become more apparent upon reading the following specification in conjunction with the accompanying drawing figures.

DETAILED DESCRIPTION OF THE INVENTION

Figure 1:
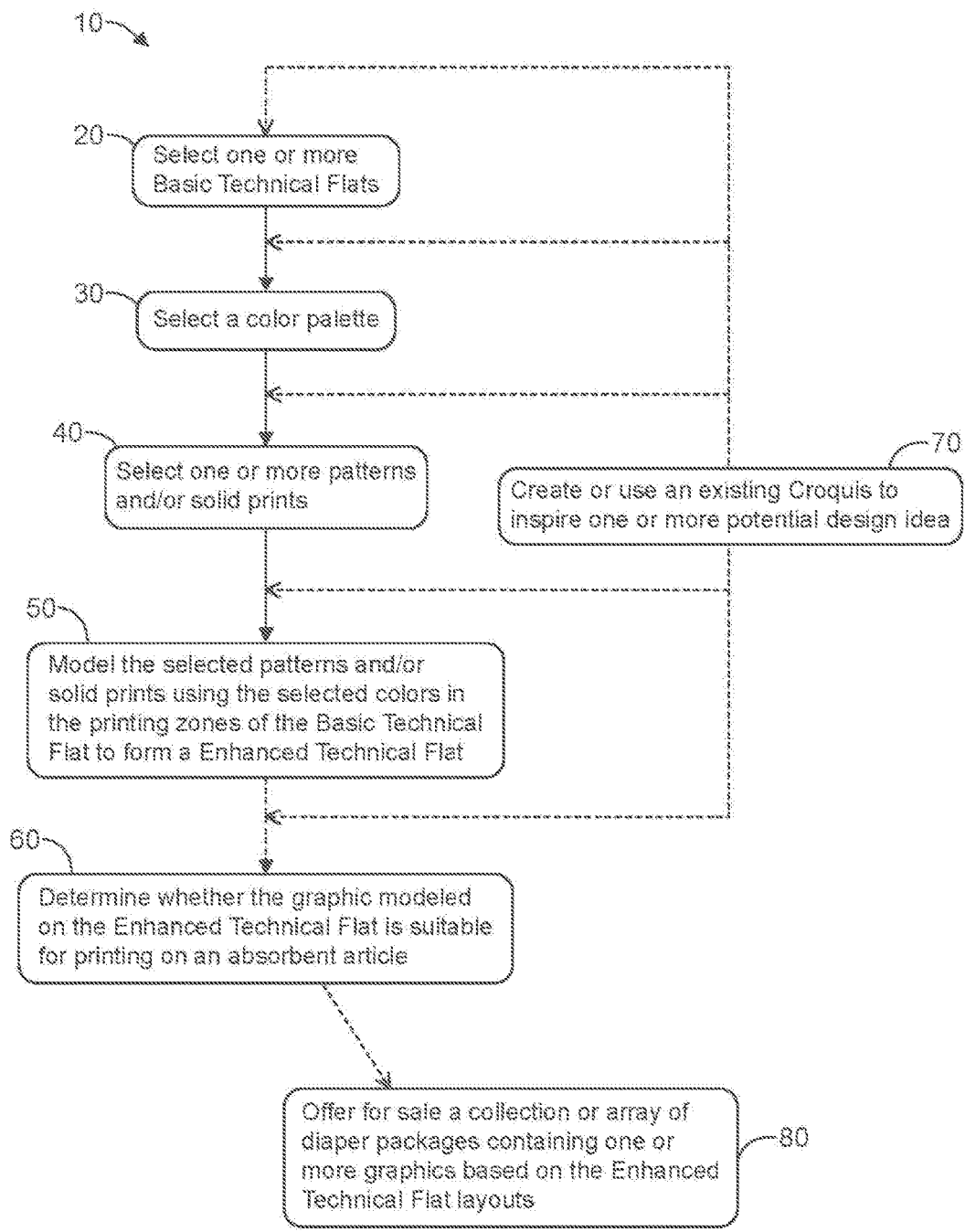
FIG. 1 is a flowchart of a method of designing graphics for absorbent articles suitable for use with the invention.

In one aspect, the invention is intended primarily for use with absorbent articles. As used herein, the term "absorbent article" refers to devices which absorb and contain body exudates, and, more specifically, refers to devices which are placed against or in proximity to the body of the wearer to absorb and contain the various exudates discharged from the body. As used herein, the term "diaper" refers to an absorbent article generally worn by infants and incontinent persons that is worn about the lower torso of the wearer. It should be understood, however, that the invention is also applicable to other absorbent articles such as incontinence briefs, incontinence undergarments, incontinence pads, diaper holders and liners, feminine hygiene garments, feminine hygiene pads, feminine hygiene pantiliners, tampons, and the like. As used herein, the term "disposable" refers to absorbent articles that generally are not intended to be laundered or otherwise restored or reused as absorbent articles, i.e. they are intended to be discarded after a single use, and preferably, to be recycled, composted, or otherwise disposed of in an environmentally compatible manner. In an embodiment, the absorbent articles for which the invention is primarily intended for use, are disposable absorbent articles.

In an embodiment of the invention, the method described herein is used to create a graphic for an absorbent article. In another embodiment, the method is used to create several similar and/or related graphics for a set of absorbent articles. In yet another embodiment, the absorbent articles forming such set are offered for sale together as a set.

Absorbent articles may typically comprise a topsheet having a body facing surface and a garment facing surface, a backsheet having a bodyfacing surface and a garment facing surface, and an absorbent core disposed between the garment facing surface of the topsheet and the bodyfacing surface of the backsheet. In an embodiment, the graphics created by the method disclosed herein are disposed upon the bodyfacing surface of the topsheet. In another embodiment, the graphics are disposed upon the garment facing surface of the topsheet. In another embodiment, the graphics are disposed upon the garment facing surface of the backsheet. In yet another embodiment, the graphics are disposed upon both the bodyfacing surface of the topsheet and the garment facing surface of the backsheet. Other absorbent articles, e.g. catamenial tampons, may typically comprise a compressed absorbent core disposed within an overwrap substantially covering the exterior surface of the compressed absorbent core, the overwrap having a core facing surface and a bodyfacing surface. In an embodiment, the graphics created by the method disclosed herein are disposed upon the core facing surface of the overwrap. In another embodiment, the graphics are disposed upon the bodyfacing surface of the overwrap. In yet another embodiment, the graphics are disposed upon both the core facing surface of the overwrap and the bodyfacing surface of the overwrap. In an embodiment, the overwrap comprises a non-woven material.

As shown in FIG. 1, a method of designing graphics for absorbent articles 10 is provided. According to method 10, in step 20, one or more basic technical flats 90 is selected, in step 30, a color palette is selected, in step 40, one or more patterns and/or solid prints is selected, in step 50, the selected patterns and/or solid prints, using the selected colors, are modeled in the printing zones 94 of the basic technical flat 90 to form an enhanced technical flat 100. At this point, a graphic for an absorbent article has been designed. These steps and additional optional steps are discussed in more detail herein. It is to be noted that, as depicted in FIG. 1, an embodiment provides that step 30 occurs prior to step 40. However, it will be appreciated by the skilled person that in another embodiment, step 40 occurs prior to step 30, and in yet another embodiment, steps 30 and 40 are performed concurrently.

Figure 2:
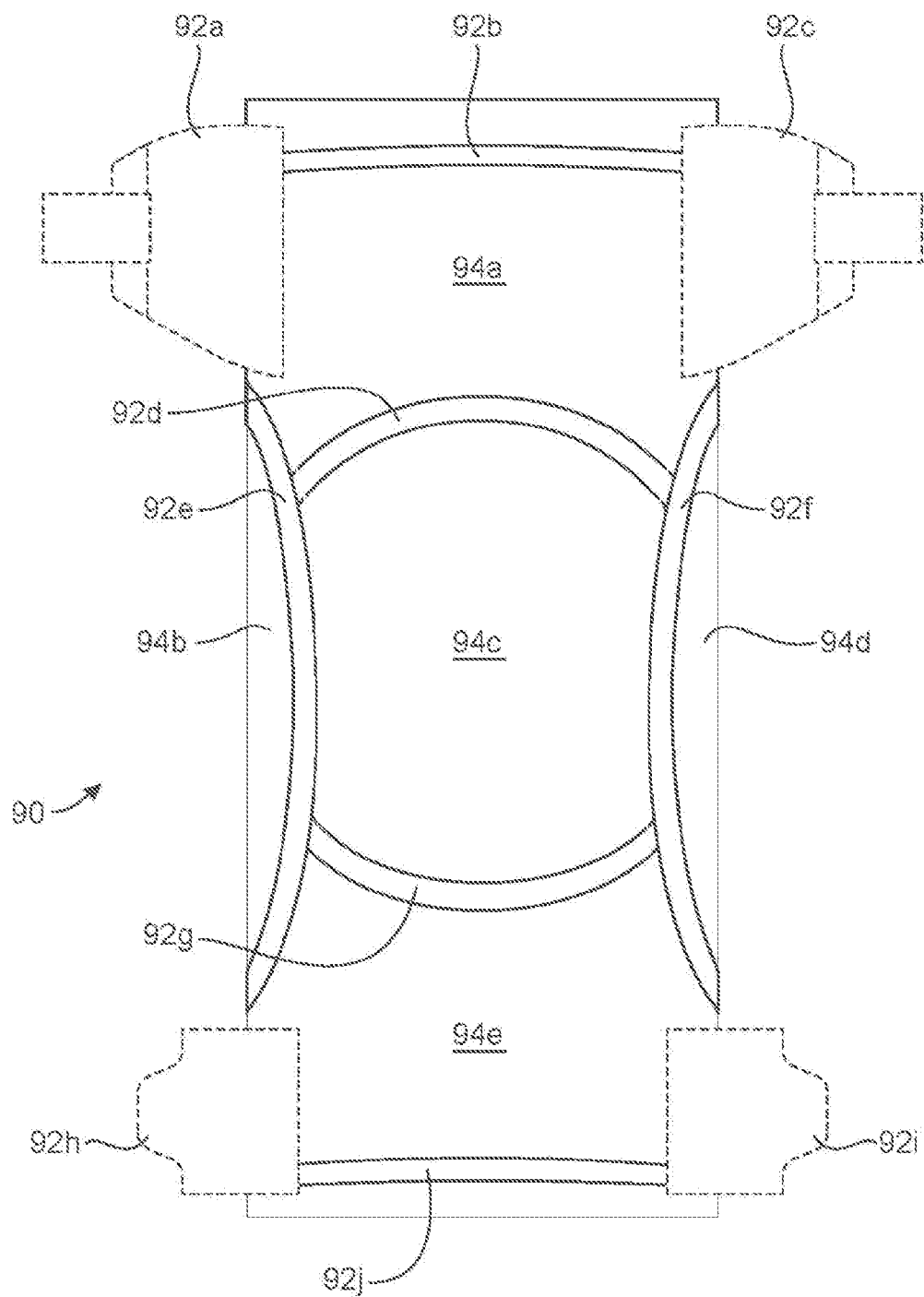
FIG. 2 is a perspective view of a basic technical flat employed in an embodiment of a method of designing graphics for absorbent articles suitable for use with the invention.

In step 20, one or more basic technical flats 90 is selected. A basic technical flat 90 is a drawing showing the general outline and visible physical features of an absorbent article, a non-limiting example of which is shown in FIG. 2. A basic technical flat 90 may be hand drawn, but is typically mechanically or digitally drawn, thus making it easier to store, transfer to others, and reproduce in mass. A basic technical flat 90 will typically show design elements 92 of the absorbent article. Design elements 92 may be physical features of the absorbent article, such as the overall outline, location of tabs, fasteners, borders, junctions of materials, stitching, and like elements. A basic technical flat 90 may also show some design elements 92 that are either actual physical features of the absorbent article or that are not actual physical features but are to be printed on the absorbent article to make it appear that they are actual elements of the absorbent article, non-limiting examples of features that may fall within either or both of these groups include: printing borders, seams, pockets, zippers, zipper flaps, topstitching, embossment, quilting, buttons, bows, ribbons, straps, snaps, belt loops, suspenders, sales tags, etc. Basic technical flat 90 comprises defined printing zones 94 for which colors and patterns and/or solid prints will be selected for in later steps. Such printing zones 94 may optionally be shaded, hatched, or otherwise detailed to impart an appearance of being 3-dimensional. Typically, a basic technical flat 90 will comprise a plurality of printing zones 94, depending on how many permutations are desired to be available for selection in the final graphic. The printing zones 94 define areas where graphics will be printed on the absorbent articles. Preferably, the basic technical flat 90 comprises from 2 to 8, more preferably from 4 to 6, printing zones. The basic technical flat shown in FIG. 2 has 10 design elements 92a to 92j, and 5 printing zones 94a to 94e.

In step 20, a single basic technical flat 90 may be selected, or to increase the number and variety of graphics being created at once, several basic technical flats 90 may be selected. For example, the selection of multiple basic technical flats 90 may enable one designer to progress several artistic creations concurrently, thereby avoiding the stymie of creative thought that may be associated with following a one-process-at-a-time approach. Similarly, the selection of multiple basic technical flats 90 may enable several designers to progress several artistic creations concurrently and yield a variety of graphics for comparison and/or advancement to finality. Where multiple basic technical flats 90 are available, they will typically exhibit different features of the same absorbent article for which graphics are being designed, or they will exhibit features of different absorbent articles for which graphics are being designed. Accordingly, it is contemplated that similar and/or related graphics could be designed using method 10 for a variety of different absorbent articles in a product line, e.g. diapers and pants, or feminine pads and pantiliners.

In step 30, a color palette is selected. Preferably, the colors are complementary to each other and to the patterns and/or solid prints selected in step 40. By complementary, it is meant that a designer believes they work together to achieve a common artistic theme or expression, noting that such theme may be one of intentional contrast. It is not intended that they must be classically accepted by the general population as "going together". For example, a designer may select a color palette in which the colors appear to clash to the ordinary observer, but upon further investigation, reveal a psychedelic color scheme.

In step 40, one or more patterns and/or solid prints is selected. Preferably, the patterns and/or solid prints are complementary to each other and to the colors selected in step 30. As with the colors, complementary means that the designer believes that they work together to achieve a common artistic theme or expression, noting that such theme may be one of intentional contrast. In an embodiment, the patterns and/or solid prints are obtained from a print house, a print designer, or a fabric pattern designer.

For each of steps 30 and 40, the colors and the pattern and/or solid print, respectively, may be independently selected from themed or otherwise like groups of colors and patterns and/or solid prints. In an embodiment, they may be selected from groups being categorized as being gender neutral, boy appropriate, or girl appropriate. In another embodiment, they may be selected from groups categorized as being sporty, outdoors, sophisticated, professional, casual, cute, sassy, feminine (e.g. quilted, paisley, curly cues, polka dots), fresh, seasonal (e.g. spring, summer, fall, winter), patriotic, weather/climatic (e.g. sunny, rainy, snowy), ethnic, soft tones, earth tones, pastels, rock 'n roll, western (e.g. cowboy/cowgirl), animal, plant, food, or industrial.

Figure 3:
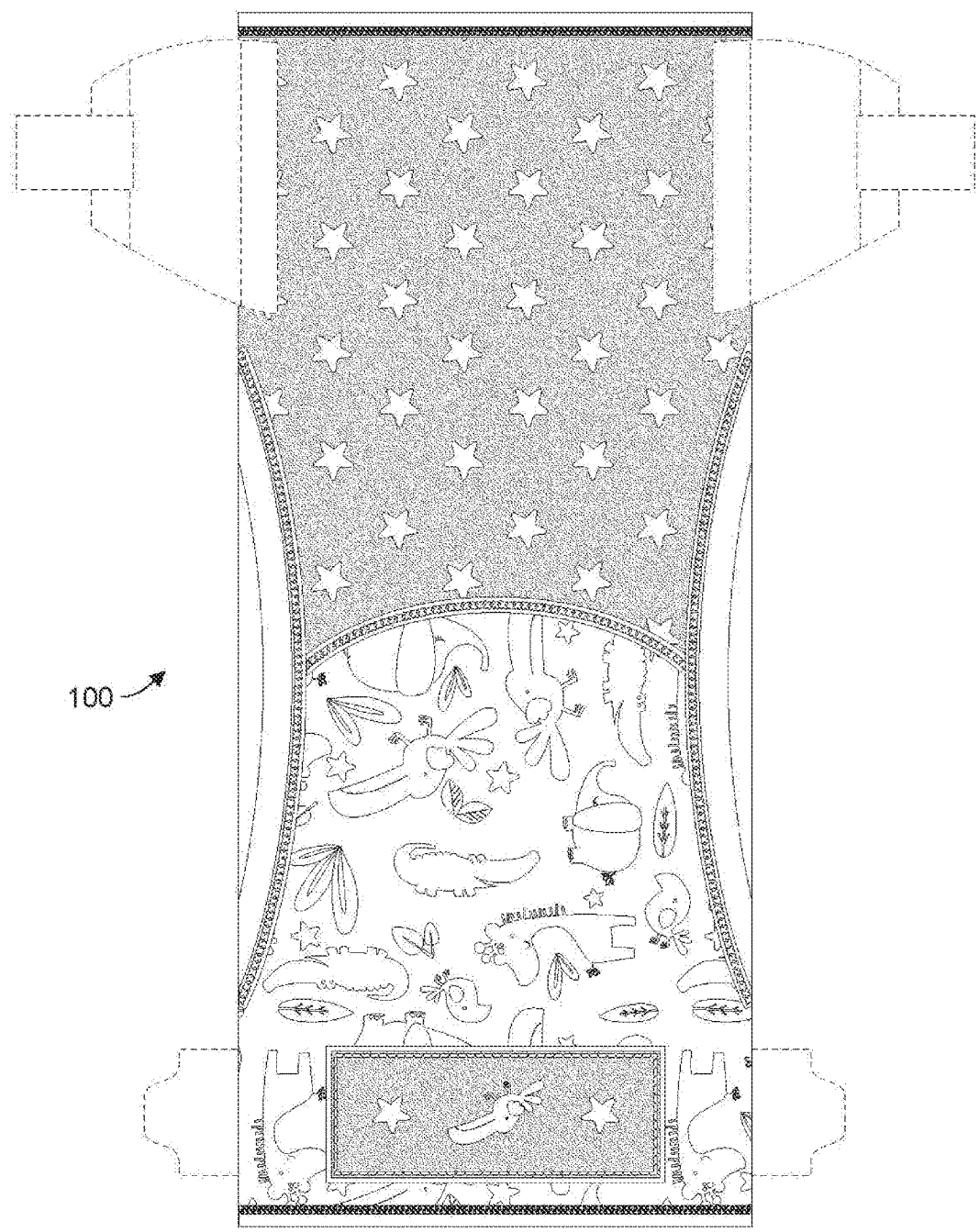
FIG. 3 is a perspective view of an enhanced technical flat employed in an embodiment of a method of designing graphics for absorbent articles suitable for use with the invention.

In step 50, the selected patterns and/or solid prints, using the selected colors, are modeled in the printing zones 94 of the basic technical flat 90 to form an enhanced technical flat 100, as shown in FIG. 3, where color is depicted by shading. An enhanced technical flat 100 is a basic technical flat 90 upon which the designer's selections in steps 30 and 40 are matched up with the printing zone that the designer selected them for, whereby the full graphic is created. Modeling may be achieved by such simple means as placing hard copy colored patterns and/or solid prints onto a hard copy basic technical flat 90, or may be achieved by more technical means, including printing on paper or another substrate including materials used in absorbent articles, and/or computer modeling. Modeling may also be achieved by creating a physical prototype of the absorbent article exhibiting all or a portion of the graphic. Any means sufficient for appreciating the final graphic may be used.

Optionally, step 60 may follow step 50. In step 60, a determination is made whether the graphic modeled on the enhanced technical flat 100 is suitable for printing on an absorbent article. It will be appreciated that there are various and many technical hurdles to be overcome when transferring a graphic from the design stage to actually disposing it upon, e.g. printing it onto, an absorbent article, a non-limiting example of which is the difficulty in registering the design to the portion of the material that it is being printed on. It will also be appreciated that due to the wide range of expression and interpretation of such expression in the fashion realm, a graphic that appears suitable to one person may not appear suitable to another. As such, there are many reasons why a graphic may need to be revised before becoming final. In the event that it is determined in step 60 that the graphic requires revision, then the graphic may be returned to any of steps one of steps 20, 30, 40, 50, or 60, of method 10.

Advantageously, due to the unexpected "assembly line" nature of method 10, unexpected at least because the designing process in the fashion realm is not intuitively a good candidate for processes typically applied to more mechanical or technical actions, the graphic may be revised to overcome the objectionable feature relatively quickly and without significant re-work. For example, if the graphic created in step 50 is of acceptable pattern but objectionable color, the designer may return to step 30 and consider selecting other color palettes, and then proceed with the remaining steps of method 10 again until a modified graphic is created in step 50. Then, step 60 may be reapplied and a new determination made of whether this modified graphic is acceptable, and so on. Yet another advantage of method 10 is that the work product created at each step may be saved for future reference or use, again minimizing re-work, and hence, saving time and cost.

Figure 4:
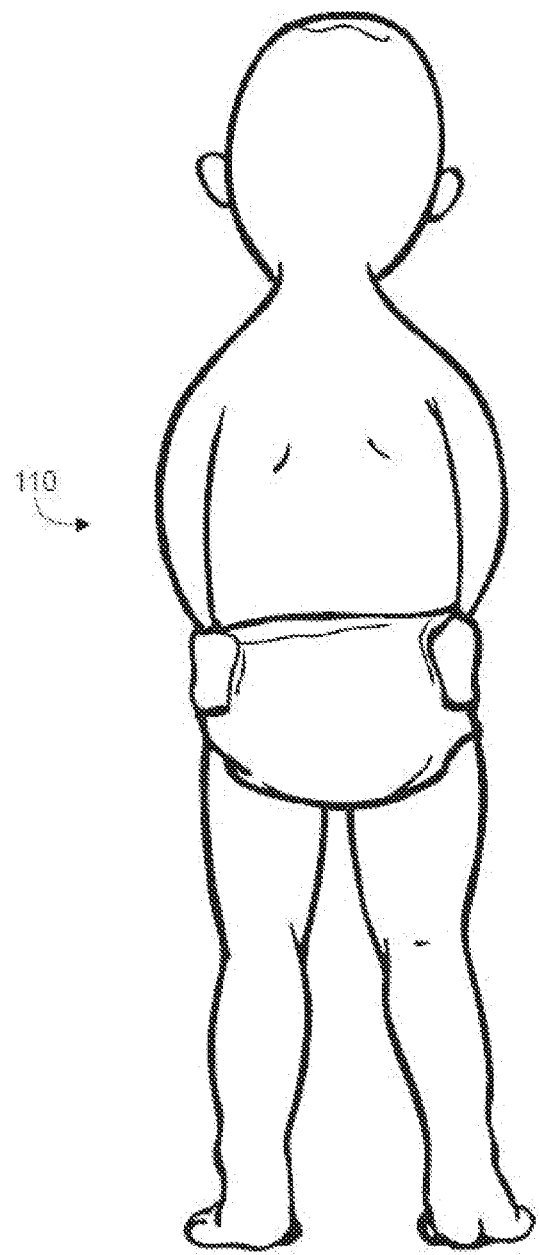
FIG. 4 is a perspective view of a croquis employed in an embodiment of a method of designing graphics for absorbent articles suitable for use with the invention.
Figures 5A, 5B:
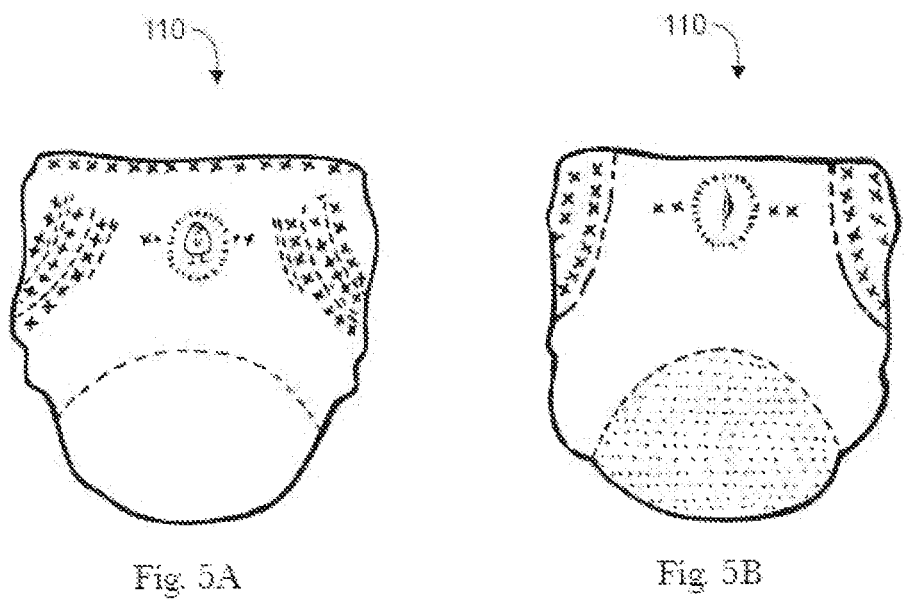
FIGS. 5a and 5b are perspective views of a pair of croquis employed in an embodiment of a method of designing graphics for absorbent articles suitable for use with the invention.

Optionally, step 70 may precede any one of steps 20, 30, 40, 50, or 60, of method 10. In step 70, a croquis is created or an existing croquis is used, to inspire one or more potential design ideas. A croquis 110 is a sketch showing very general outline and few basic physical features of an absorbent article, non-limiting examples of which are shown in FIGS. 4, 5a, and 5b. A croquis 110 is typically hand drawn, but may be mechanically or digitally drawn, thus making it easier to store, transfer to others, and reproduce in mass. A croquis 110 will typically show such features of the absorbent article as the overall outline, the location of only a few features, e.g. fasteners, borders, and like elements. A croquis 110 may show a simple version of the wearer of the absorbent article, as is shown in FIG. 4. Alternately, a croquis 110 may omit the wearer and focus more on the basic views, e.g. front and back as worn, of the absorbent article without regard to many technical features, as is shown in FIGS. 5a and 5b. A croquis 110 may be in black and white, or in color, and either way, may optionally be shaded, hatched, or otherwise detailed to impart an appearance of being 3-dimensional.

The skilled person will create or select a created croquis 110 with sufficient detail about the features of the absorbent article corresponding to the step of method 10 for which the croquis 110 is being used to inspire one or more potential design ideas. For example, a croquis 110 used prior to step 20 may look more like the croquis 110 shown in FIG. 4, which provides very little detail about the features of the absorbent article, e.g. the general shape of the absorbent article when seen from the back of the wearer, the location of two fasteners, and some shading to impart 3-dimensional appearance. However, a croquis 110 used prior to either or both of steps 30 and 40 may look more like the croquis 110 shown in FIGS. 5a and 5b, which still provide little detail about the features of the absorbent article, e.g. a 2-dimensional view of the general shape of the absorbent article when seen from both the front and back of the wearer, without the wearer present, and the location of two fasteners, but do provide more detail about the possible colors and patterns that may be employed in the ultimately designed graphic.

In an embodiment, a method of selling co-packaged sets of absorbent articles bearing similar and/or related graphics 200 is provided. It should be understood that method 200 relates to the offer to sell such absorbents articles as well as actually selling them. The skilled person will appreciate that such absorbent articles may be advantageously designed by using method 10. A suitable method for use with the present invention is disclosed in commonly assigned, co-pending U.S. Ser. No. 12/835,188, entitled "Method of Designing Graphics for Absorbent Articles", filed on 13 Jul. 2010.

According to method 200, absorbent articles bearing similar and/or related graphics are packaged together and sold. "Similar and/or related" refers to a degree of sameness of at least some of the elements of the graphics embodied two or more absorbent articles. It is not intended to mean that two or more graphics being compared are identical except for scale, e.g. due to the sizes of the various absorbent articles being different. Elements to consider in determining similarity and/or relatedness include but are not limited to: color palettes (such as described in step 30 of method 10), patterns and/or solid prints (such as described in step 40 of method 10), shapes, themes, voids, position, orientation, and the like; preferably color palettes and patterns and/or solid prints are considered.

Figure 6A:
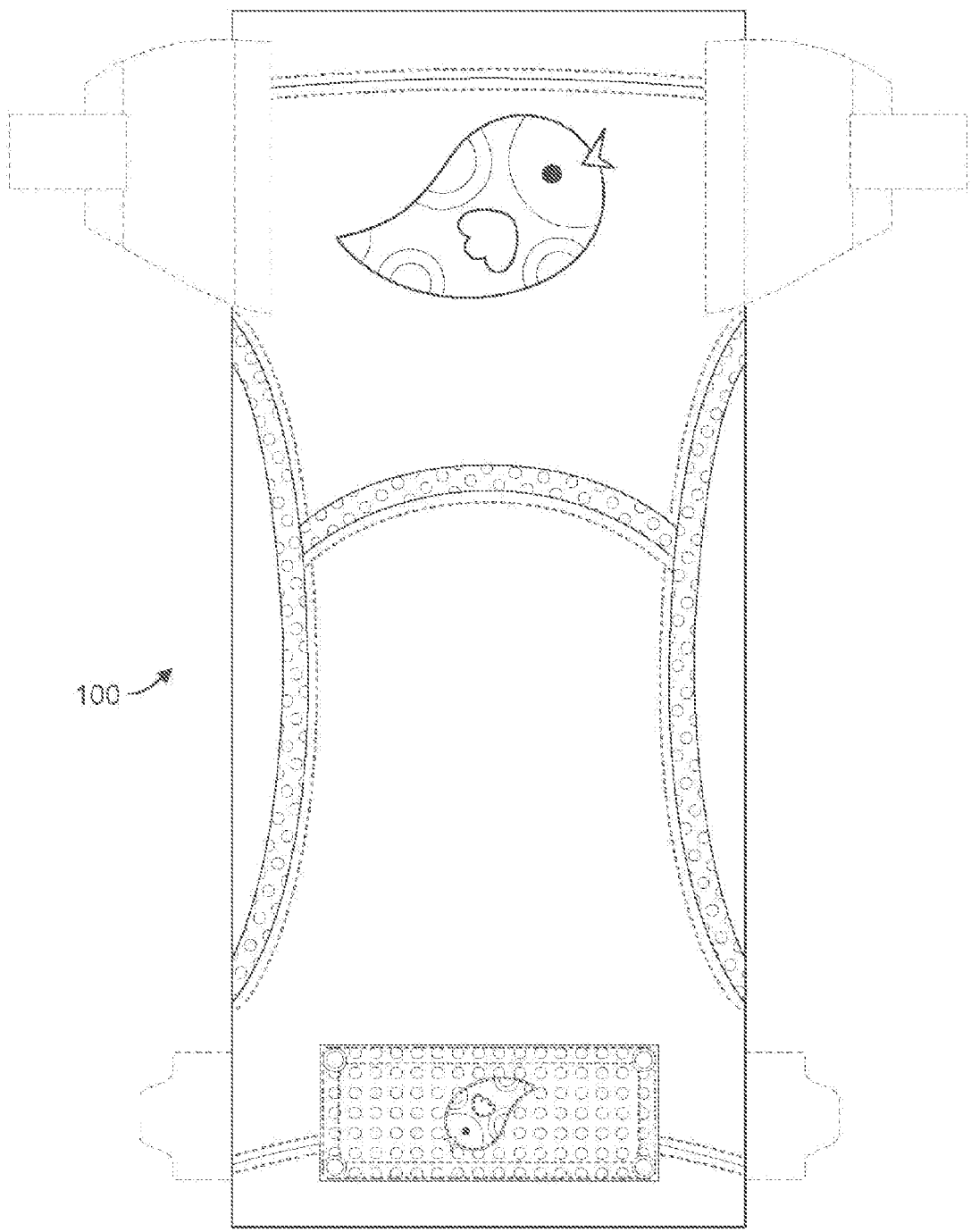
FIGS. 6a and 6b are perspective views of two graphics employed in an embodiment of the invention.
Figure 6B:
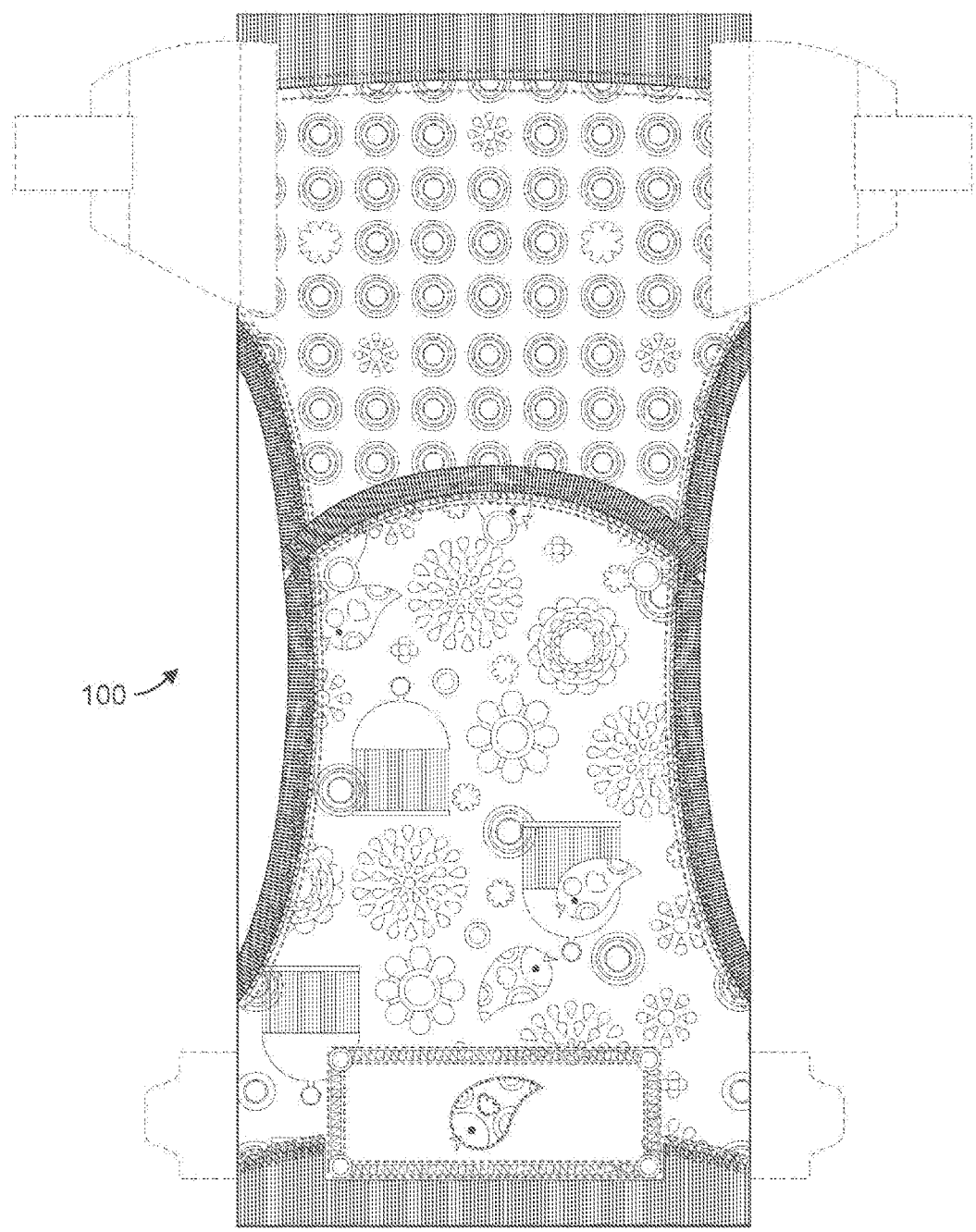

As shown in FIGS. 6a and 6b, graphics that are similar and/or related may share a common color palette, common elements, e.g. birds, common positioning of areas that are printed vs. non-printed, and common placement of actual or apparent stitching. In an embodiment, as shown in FIGS. 6a and 6b, the array of absorbent articles may bear similar and/or related graphics where one absorbent article (e.g. one bearing the graphic shown in FIG. 6a) may exhibit a simple and plain look about it, e.g. having a significant amount of unprinted space and basic graphics, whereas another absorbent article (e.g. one bearing the graphic shown in FIG. 6b) may exhibit substantially more complex graphics that include additional patterns not seen in the other absorbent article, but still keeping within, e.g. the same theme. Such an array may be characterized as a "collection" of absorbent articles.

Figure 7A:
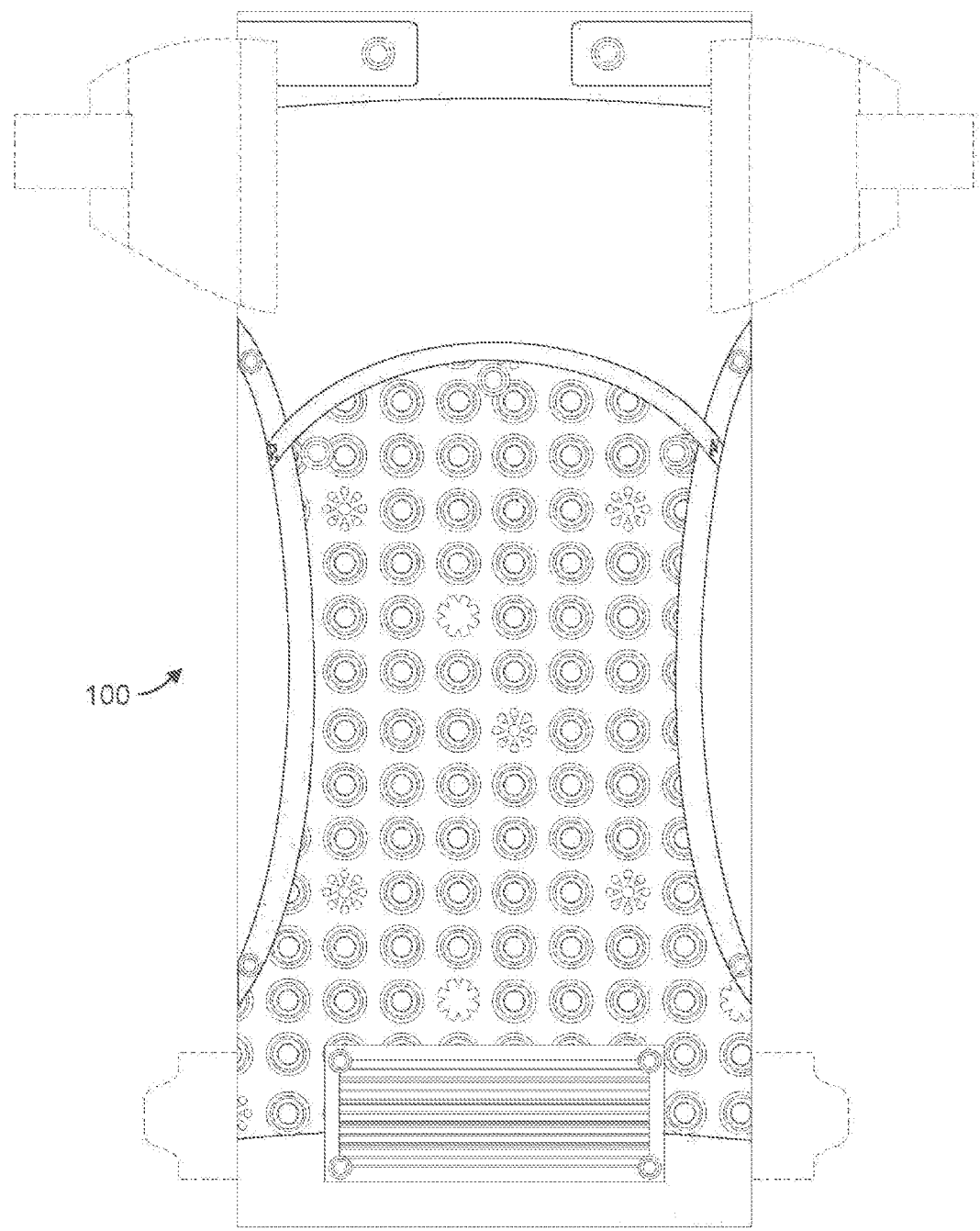
FIGS. 7a, 7b, and 7c are perspective views of three graphics employed in an embodiment of the invention.
Figure 7B:
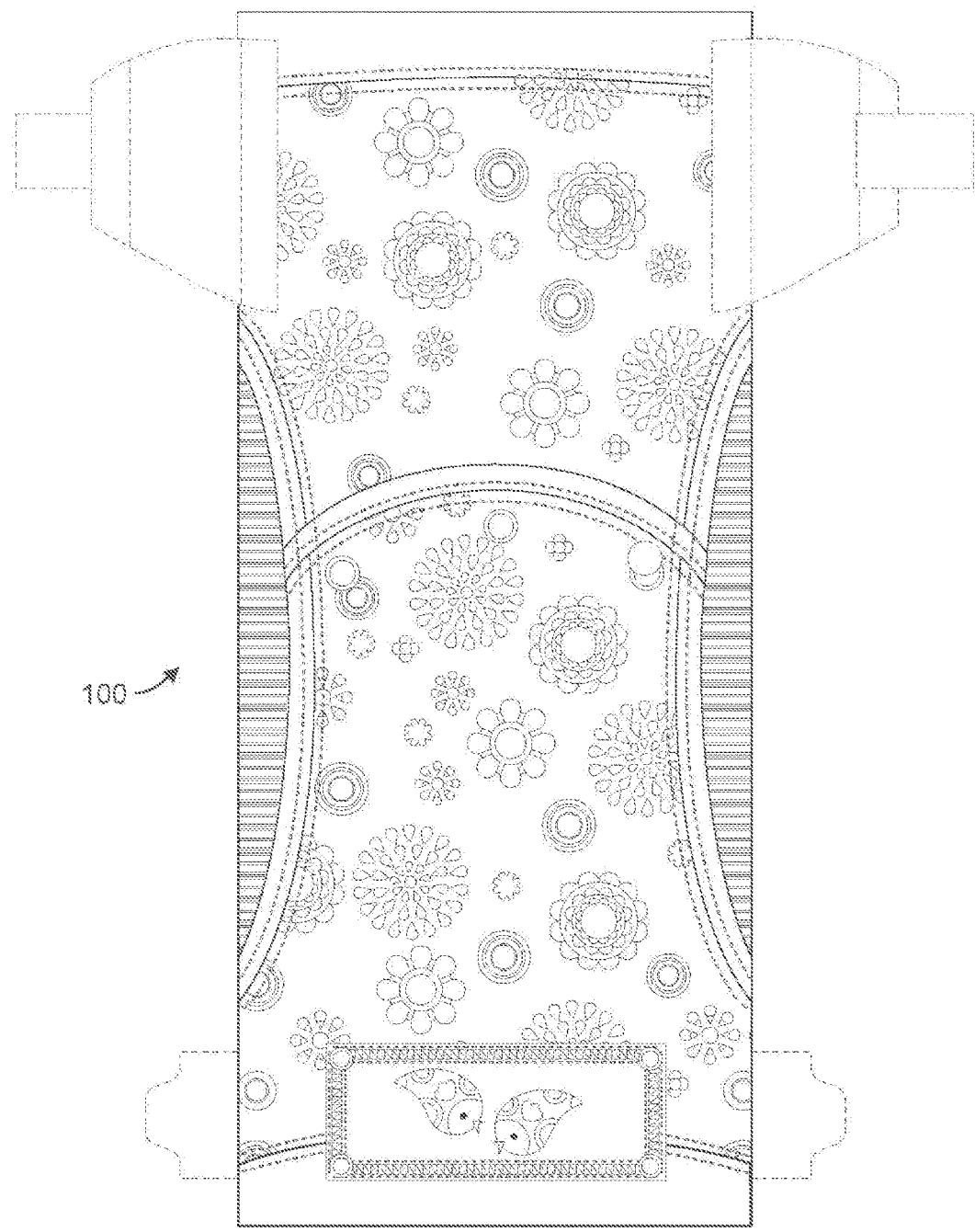
Figure 7C:
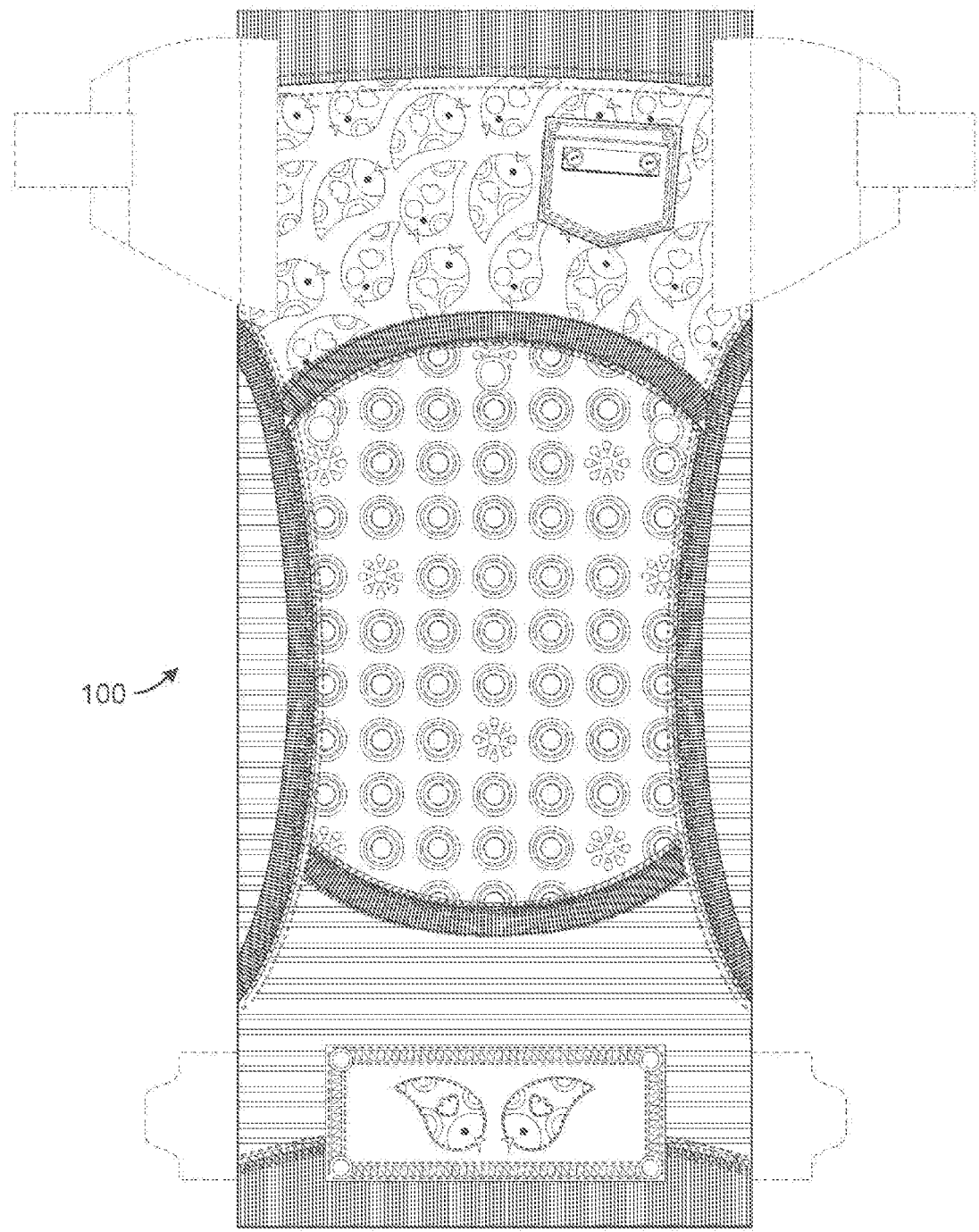

As shown in FIGS. 7a, 7b, and 7c, graphics that are similar and/or related may share a common color palette, common use of concentric circles, common lined patterns, common elements, birds, and common positioning of areas that are printed vs. non-printed. In another embodiment, as shown in FIGS. 7a, 7b, and 7c, the array of absorbent articles may bear similar and/or related graphics where one absorbent article (e.g. one bearing the graphic shown in FIG. 7a) may exhibit a simple look about it, e.g. having two main patterns with some bordering, whereas another absorbent article (e.g. one bearing the graphic shown in FIG. 7b) may exhibit somewhat more complex graphics that include additional patterns not seen in the other absorbent article, but still keeping within, the same theme, and yet another absorbent article (e.g. one bearing the graphic shown in FIG. 7c) may exhibit yet more complex graphics that combine various elements from the other two absorbent articles and added a further feature, e.g. the pocket, but still keeping within, e.g. the same theme. It is to be noted that the color palette is common across all three absorbent articles. Such an array may also be characterized as "collection" of absorbent articles.

Collections of absorbent articles comprise a plurality of design graphics, preferably from 2 to 6, more preferably from 2 to 4. It is contemplated that an entire collection or fewer than an entire collection may be sold contemporaneously. Preferably, absorbent articles bearing from 2 to 4, more preferably from 2 to 3, design graphics are co-packaged. Co-packaged means sold together at the same time. This may be accomplished, e.g. in store, by actually placing the similar and/or related graphic absorbent articles in the same primary package, e.g. a polybag made of, e.g. polyethylene, polypropylene, or mixtures or laminates thereof, by placing them in separate primary packages that are then placed together into a secondary package, e.g. a cardboard box containing both polybags, by securing separate primary packaging to each other, e.g. adhesive or physical binding means, e.g. string or tape, or other suitable means for ensuring that the absorbent articles are sold ultimately as a unit. Accordingly, in an embodiment, method 200 may provide for: (a) selecting a plurality of design graphics from a collection of similar and/or related graphics; (b) printing sets of absorbent articles, each bearing a different design graphic selected in the previous step; (c) co-packaging the sets of absorbent articles; and (d) offering the co-packaged sets for sale. The skilled person will appreciate that in the embodiment just described, any or all of the steps typically carried, out by a manufacturer or a retailer of the absorbent articles, may be performed by an agent or designee thereof.

This may be accomplished, e.g. online, by making available any of the aforementioned co-packaged executions, by allowing a purchaser to "click on" combinations that will ultimately be co-packaged prior to shipping to the purchaser, or other suitable means for ensuring that the absorbent articles are sold ultimately as a unit. It is contemplated that by allowing a purchaser to "click on" combinations that will ultimately be co-packaged prior to shipping to the purchaser, a significant degree of customization of the order may take place. Accordingly, in an embodiment, method 200 may provide for: (a) a manufacturer or a retailer, allowing a purchaser to select a plurality of design graphics from a collection of similar and/or related graphics; (b) the manufacturer printing sets of absorbent articles, each bearing a different design graphic selected by the purchasers; (c) the manufacturer co-packaging the sets of absorbent articles; and (d) making the co-packaged sets available to the purchaser. The skilled person will appreciate that in the embodiment just described, any or all of the steps being carried out by a manufacturer or a retailer, or even a purchaser, may be performed by an agent or designee thereof. Furthermore, the step of making available to the purchaser may include sending the sets of absorbent articles to a benefactor of the purchaser, e.g. as a gift.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed, or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of selling co-packaged sets of absorbent articles bearing similar and/or related graphics comprising the steps of:
    a) designing graphics for absorbent articles by:
        i. selecting one or more basic technical flats, the basic technical flats comprising the general outline and design elements of an absorbent article, and a plurality of printing zones;
        ii. selecting a color palette;
        iii. selecting one or more patterns and/or solid prints; and
        iv. modeling the one or more selected patterns and/or solid prints, using the one or more selected colors, in the printing zones of the basic technical flat that they are selected for, to transform the basic technical flat into an enhanced technical flat thereby creating the graphic;
    b) printing sets of absorbent articles, each set bearing a different design graphic designed in the previous step;
    c) co-packaging the sets of absorbent articles; and
    d) making the co-packaged sets of absorbent articles available to a purchaser.

2. The method of claim 1, wherein the similarity and/or relatedness of the graphics is exhibited in at least one element of the graphics selected from the group consisting of: color palettes, patterns and/or solid prints, shapes, themes, voids, position, and orientation.

3. The method of claim 2, wherein the similarity and/or relatedness of the graphics is exhibited in at least one element of the graphics selected from the group consisting of: color palettes, and patterns and/or solid prints.

4. The method of claim 2, wherein the color palettes, and patterns and/or solid prints are independently selected from groups categorized as being: gender neutral, boy appropriate, girl appropriate, sporty, outdoors, sophisticated, professional, casual, cute, sassy, feminine, quilted, paisley, curly cues, polka dots, fresh, seasonal, spring, summer, fall, winter, patriotic, weather, climatic, sunny, rainy, snowy, ethnic, soft tones, earth tones, pastels, rock 'n roll, western, cowboy, cowgirl, animal, plant, food, industrial, and combinations thereof.

5. The method of claim 3, wherein the similarity and/or relatedness of the graphics is exhibited in the color palettes of the graphics.

6. The method of claim 3, wherein the similarity and/or relatedness of the graphics is exhibited in the patterns and/or solid prints of the graphics.

7. The method of claim 1, wherein the similarity and/or relatedness of the graphics is the result of using the same or similar basic technical flats during the process of designing the graphics.

8. The method of claim 1, wherein the sets of absorbent articles are placed in the same primary package, placed in separate primary packages that are placed together into a secondary package, or placed in separate primary packages that are sold together with each as a unit.

9. The method of claim 8, wherein the sets of absorbent articles are placed in the same primary package.

10. The method of claim 1, wherein the absorbent articles are diapers.

11. The method of claim 1, wherein the absorbent articles are feminine pads, pantiliners, or tampons.

12. The method of claim 1, wherein the absorbent articles are incontinence pads.

13. The method of claim 1, wherein the absorbent articles each comprise a topsheet having a bodyfacing surface and a garment facing surface, a backsheet having a bodyfacing surface and a garment facing surface, and an absorbent core disposed between the garment facing surface of the topsheet and the bodyfacing surface of the backsheet, wherein the graphic is printed on a surface of the absorbent article selected from the group consisting of: the bodyfacing surface of the topsheet, the garment facing surface of the topsheet, the garment facing surface of the backsheet, and both the bodyfacing surface of the topsheet and the garment facing surface of the backsheet.

14. The method of claim 1, wherein the absorbent articles each comprise a compressed absorbent core disposed within an overwrap substantially covering the exterior surface of the compressed absorbent core, the overwrap having a corefacing surface and a bodyfacing surface, wherein the graphic is printed on a surface of the absorbent article selected from the group consisting of: the corefacing surface of the overwrap, the bodyfacing surface of the overwrap, and both the corefacing surface of the overwrap and the bodyfacing surface of the overwrap.

* * * * *